United States Patent [19]

Bissell et al.

[11] 4,388,233

[45] Jun. 14, 1983

[54] SYNTHETIC SUBSTRATES FOR ENZYME ANALYSIS

[75] Inventors: Eugene R. Bissell, Alamo; Alexander R. Mitchell, Livermore; Karen W. Pearson, Livermore; Robert E. Smith, Livermore, all of Calif.

[73] Assignee: The Regents of the University of California, Berkeley, Calif.

[21] Appl. No.: 264,118

[22] Filed: May 15, 1981

[51] Int. Cl.³ .................. C07C 103/52; C07D 311/06
[52] U.S. Cl. ............................ 260/112.5 R; 549/288; 549/280; 549/285; 548/159
[58] Field of Search .................... 260/112.5 R, 343.45; 549/288

[56] References Cited

U.S. PATENT DOCUMENTS

| | | | |
|---|---|---|---|
| 3,514,471 | 5/1970 | Yanagisawa et al. | 260/343.45 |
| 3,681,397 | 8/1972 | Knupfer et al. | 260/343.45 |
| 3,862,011 | 1/1975 | Smith | 195/103.5 R |
| 3,884,896 | 5/1975 | Blombach et al. | 260/112.5 R |
| 3,886,136 | 5/1975 | Claeson et al. | 260/112.5 R |
| 4,061,625 | 12/1977 | Af Ekenstam et al. | 260/112.5 R |
| 4,137,225 | 1/1979 | Af Ekenstam et al. | 260/112.5 R |
| 4,215,047 | 7/1980 | Sakakibara et al. | 260/343.45 |
| 4,257,939 | 3/1981 | Sakakibara | 260/112.5 R |
| 4,279,810 | 7/1981 | Claeson et al. | 260/112.5 R |

FOREIGN PATENT DOCUMENTS

| | | | |
|---|---|---|---|
| 1293160 | 4/1969 | Fed. Rep. of Germany | 549/288 |
| WO80/02295 | 10/1980 | PCT Int'l Appl. | 260/112.5 |
| 1077114 | 3/1965 | United Kingdom | 549/288 |

OTHER PUBLICATIONS

"Automated Enzyme Assays Using . . . Fluorescence Detection", K. W. Pearson, et al, preprint of paper submitted for publication, dated Aug. 6, 1980.
J. of Histochemistry and Cytochem., vol. 27, No. 11, pp. 1499–1504 (1979).
Seminars in Thrombosis and Hemostasis, vol. VI, No. 3 (1980) pp. 203–207 and 290–291.
Thrombosis Research 17:, 393–402 (1980).
Eastman Kodak Co. Catalog of Laser Dyes (1979).

Primary Examiner—Delbert R. Phillips
Attorney, Agent, or Firm—Majestic, Gallagher, Parsons & Siebert

[57] ABSTRACT

Synthetic substrates are provided which may be represented as A-D. The A moiety thereof includes an amino acid, polypeptide, or derivative thereof. The D moiety thereof includes 7-amino coumarin derivatives having an electron withdrawing substituent group at the 3 position carbon or fused between the 3 and 4 position carbons.

1 Claim, No Drawings

SYNTHETIC SUBSTRATES FOR ENZYME ANALYSIS

The Government has rights in this invention pursuant to Contract No. W-7405-ENG-48 awarded by the U.S. Department of Energy.

BACKGROUND OF THE INVENTION

1. Field of the Invention

The present invention relates generally to synthetic substrates, more particularly to synthetic substrates useful in qualitative and quantitative methods for determining proteolytic enzymes.

2. Prior Art

In recent years the study of proteinases has been greatly advanced by the recognition that construction of synthetic substrates to simulate segments of naturally occurring substrates can lead to remarkably comparable specificity of enzyme activity. Although proteins are the natural substrates for proteinases, they are often unsuitable for detecting enzyme activity or presence because they offer multiple sites for enzyme cleavage. On the other hand, synthetic substrates have well defined chemical structures and the kinetics of hydrolysis are simplified when there is only a single point of cleavage. Thus, enzyme specificity may be determined by the number and arrangement of amino acids in the peptide moiety of the synthetic substrate, and the activity of the enzyme may be measured by the amount of a detector moiety liberated upon hydrolysis of the synthetic substrate.

Particular synthetic substrates have been found useful in determinations of specific enzymes in biological fluids such as blood, serum, urine, and the like. For example, Svendsen et al reported use of synthetic substrates in the assay of thrombin and thrombin-like enzymes. "Synthetic chromogenic substrates for determination of trypsin, thrombin and thrombin-like enzymes", *Thromb. Res.*, 1:267–278 (1972). More recently, Kirchof et al have reported improvements in measuring the prothrombin concentration in plasma, using synthetic substrates, for clinical applications such as aiding in the control of anticoagulant therapy. "Control of an anticoagulant therapy with a chromogenic substrate", *Haemostasis*, 8: 1–7 (1979).

To date there are six, generally accepted detector groups for such synthetic substrates, each of which has unique properties and which may be better suited to assay a particular proteinase than the others. These six common detector groups are: para-nitroaniline; 2-naphthylamine; 4-methoxy-2-naphthylamine; 5-aminoisophthalic acid; 7-amino-4-methylcoumarin; and, 7-amino-4-trifluoromethylcoumarin. The latter five detector groups may be detected by either fluorometric or colorimetric methods. Because the chromophore, para-nitroaniline, is yellow, enzyme assays employing this chromosphere are normally colorimetric.

These known substrates for quantification of enzymes in solution, i.e., blood, serum, urine or the like, have not been satisfactory for enzyme localization within monodispersed cells. One recent report suggests that quantification of enzymes in single cells appears promising by fluorescent staining, and discloses the use of coupling 4-methoxy-2-naphthylamine to 5-nitrosalicylaldehyde. R. E. Smith and P. N. Dean, *Journal of Histochemistry and Cytochemistry*, Vol. 27, No. 11, pp. 1499–1504 (1979).

The identification and quantification of proteinases in single cells holds great potential for applications such as diagnosing disease states, but to date has been hindered by the lack of suitable detector groups. This is believed due at least in part to the solubility of the known detector groups which, when liberated from the synthetic substrates, have tended to permeate the cell membrane rather than remain localized within the cell.

SUMMARY OF THE INVENTION

Accordingly, it is an object of the present invention to provide a synthetic substrate suitable for use in qualitative and quantitative methods of determining proteolytic enzymes, and particularly a synthetic substrate useful for enzyme analyses by fluorometric techniques.

It is a further object of the present invention to provide a synthetic substrate useful for determinations of specific enzymes in biological fluids and/or in monodispersed, active cells.

In one aspect of the present invention, a synthetic substrate is generally represented by A-D where the A and D moieties of a A-D are bonded together by a hydrolyzable bond. The A moiety includes an amino acid, a peptide, or a derivative thereof. The D moiety is a coumarin derivative having an electron withdrawing group substituted at the 3 position carbon or fused at the 3 and 4 position carbons.

A one preferred embodiment in accordance with the present invention has the structure

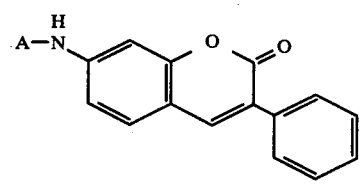

This embodiment provides a striking increase in fluorescent intensity, by comparison with known coumarin derivative synthetic substrates, when utilized for assying enzymes by fluorometric techniques.

Synthetic substrates in accordance with the present invention preferably yield liberated detector compounds therefrom which fluoresce at wavelengths of at least about 460 nm, yield a relatively intense level of fluorescence, and are relatively insoluble.

Other aspects and advantages of the invention will become apparent from the following description and appended claims.

DETAILED DESCRIPTION OF THE PREFERRED EMBODIMENTS

Broadly, a synthetic substrate in accordance with the present invention includes a coumarin derivative. The basic coumarin structure and conventional ring numbering thereof is

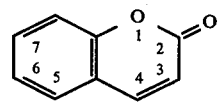

A synthetic substrate in accordance with the present invention includes a coumarin derivative having an amido amino group at the 7 position carbon. The inventive synthetic substrate will hereinafter frequently be generally represented as A-D (hereinafter further described), or as the FIGS. 1A and 1B structures, below.

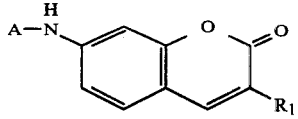

FIG. 1A

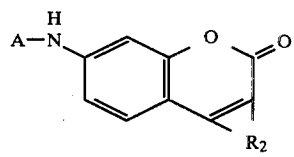

FIG. 1B

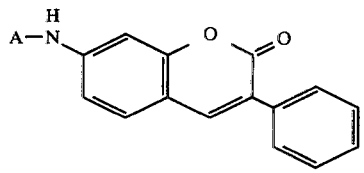

FIG. 2

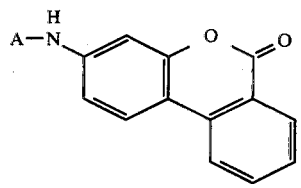

FIG. 3

In both representations A-D and the FIGS. 1A, 1B structures, above, the A moiety is an amino acid, a polypeptide, or a derivative of the amino acid or of the polypeptide. The A moiety will first be more fully described, and then the D moiety and its substituents at $C_3$ ($R_1$) or the fused group at $C_3$-$C_4$($R_2$) will be more fully described.

The number and sequence of amino acids of the A moiety determine the enzyme specificity for the synthetic substrate. Substantially any combination of amino acids may be utilized to obtain the desired specificity. Where the A moiety is a polypeptide, the amino acids thereof are linked sequentially by peptide bonds. The A moiety preferably consists of from about 1 to about 6 amino acids, as described hereinafter.

The A moiety may be in derivative form rather than in the free base form, for example various salts such as hydrobromide, hydrochloride and the like. Alternatively, the amino acid or terminal amino acid of the polypeptide may be derivatized by reaction with any suitable blocking group, such as carbobenzoxy (CBZ), benzoyl, t-Butyloxycarbonyl (BOC), p-Toluenesulfonyl (TOS), D-isomers of naturally occurring L-amino acids, and the like. Such derivative forms are useful, for example, in increasing the solubility of the synthetic substrate and/or increasing enzyme sensitivity thereto.

Thus, the A moiety may be substantially tailor-made for particular proteolytic enzymes.

The D moiety of the inventive synthetic substrate has a suitable electron withdrawing substituent on the coumarin nucleus located at the 3 position carbon (e.g. $R_1$ of the FIG. 1A structure) or fused at the 3 and 4 position carbons (e.g. $R_2$ of the FIG. 1B structure). Suitable substituents at both $C_3$ and $C_3$-$C_4$ are characterized by being electron withdrawing and by not quenching fluorescence. The electron withdrawing group substituted at $C_3$ or fused at $C_3$-$C_4$ may be a cyclic group. More particularly, the electron withdrawing group substituted at $C_3$ or fused at $C_3$-$C_4$ may be an aromatic or heterocyclic group. A preferred group fused at $C_3$-$C_4$ is benzo. Most preferably, the coumarin derivative of the D moiety has a substituent at the $C_3$ which is selected from phenyl, substituted phenyl, thiazolidyl, benzothiazolidyl or substituted benzothiazolidyl.

Two preferred embodiments of the synthetic substrates in accordance with the present invention are illustrated by FIGS. 2 and 3, below.

Synthetic substrates in accordance with the present invention may include coumarin derivatives having various organic radicals substituted at ring locations in addition to the necessary $C_3$ or $C_3$-$C_4$, so long as such organic radicals do not quench fluorescence. For example, these other substituents may be located at $C_4$ (where the coumarin derivative has the electron withdrawing group at $C_3$), or at $C_5$. In the former situation, such an organic radical will sometimes hereinafter be represented as $R_3$, and in the later as $R_4$. Among the various organic radicals which may optionally be present, but which do not quench fluorescence, are alkyl, substituted alkyl, alkoxyl, aryl and heterocyclic.

The A and D moieties are bonded together by an enzyme hydrolyzable bond between the amino group at $C_7$ of the coumarin nucleus and the A moiety. In other words, the D moiety of the synthetic substrate replaces those amino acids connected to the amino portion of the peptide bond which would be hydrolyzed in natural enzyme substrates. Thus, the D moiety forms an acylamide bond with the C-terminal of the peptide. This substitution of the D moiety gives an enzyme being assayed an illusion of an extended peptide. The A moiety preferably contains not more than about 6 amino acids (unless a proline is placed near the middle), because otherwise the enzyme may cleave, or hydrolyze at one or more bonds between amino acids in the chain in addition to the desired cleavage between the $C_7$ amino group and A moiety bond.

ENZYME STUDIES

In use for enzyme analysis, following enzyme cleavage of the bond between the $C_7$ amino group and the A moiety, a detector group is liberated. This detector group is substantially identical to the precursor D moiety (although the amido group at $C_7$ is converted to a primary amino group) and shall be hereinafter referred to as the liberated D compound.

The liberated D compounds from the above-described inventive synthetic substrates generally fluoresce strongly in the blue to yellow region of the spectrum once irradiated with ultraviolet light, whereas the intact synthetic substrates of the present invention fluoresce more weakly and at shorter wavelengths. The presence of the liberated D compound can be qualitatively or quantitatively determined fluorometrically, or may be utilized in colorimetric assays. Synthetic substrates in accordance with the present invention preferably fluoresce at wavelengths of at least about 460 nm. The FIG. 2 structure, for example, yields a liberated D compound which fluoresces at a wavelength of 472 nm, and the FIG. 3 structure at a wavelength of 505 nm.

The inventive synthetic substrates may be used in enzyme kinetic studies. Table I, below illustrates kinetic data of several synthetic substrates in accordance with the present invention (where the liberated D compound is 7-amino-3-phenylcoumarin) with 3 different enzymes.

TABLE I

| A moiety | Enzyme (pH) (concentration) | $K_m$ (nmol) (std error) | $V_{max}$ (nmol/min) (std error) |
|---|---|---|---|
| Lys—Ala | DAP II[a] (5.6) | 0.321 (0.029) | 0.346 (0.012) |
| CBZ—Arg | Trypsin (8.0) (200 ng/mL) | 0.574 (0.175) | 1.264 (0.203) |
| Benzoyl—Arg | Trypsin (8.0) (200 ng/mL) | 0.945 (0.155) | 0.414 (0.043) |
| pNO$_2$CBZ—Arg | Trypsin (8.0) (200 ng/mL) | 0.193 (0.019) | 0.174 (0.009) |
| CBZ—Gly—Gly—Arg | Urokinase (8.0) (2.5 Plough units/ml) | 0.411 (0.041) | 0.137 (0.006) |

[a]Rat pituitary homogenate at a concentration of 13.75 μg/mL protein equivalent.

Table II, below, tabulates the data from three Lineweaver-Burk plots of reaction rate studies utilizing several of the inventive synthetic substrates.

TABLE II

| | 1/S (mm)$^{-1}$ | 1/V (nmol/ml/min)$^{-1}$ |
|---|---|---|
| (1) Substrate: Z—Gly—Gly—Arg—7-amino-3-phenylcoumarin | 1 | 11 |
| Enzyme: urokinase | 2 | 13 |
| | 3.5 | 17 |
| Conditions: | 5 | 22 |
| pH8, 37° C. | 8.25 | 36 |
| $E_x$ = 410 nm | 11 | 42 |
| $E_m$ = 475 nm | 12.25 | 50 |
| | 14.25 | 51 |
| (2) Substrate: | 1.7 | 1.45 |
| TOS.Z—Arg—7-amino- | 3.3 | 2.25 |
| 3-phenylcoumarin | 6.7 | 4.3 |
| | 12.5 | 7.6 |
| Enzyme: | 16.6 | 10.2 |
| trypsin | | |
| Conditions: | | |
| pH8, 37° C. | | |
| $E_x$ = 420 nm | | |
| $E_m$ = 485 nm | | |
| (3) Substrate: | 1.1 | 4.9 |
| HCl.BZ—Arg—7-amino- | 1.7 | 6.0 |
| 3-phenylcoumarin | 3.4 | 10.0 |
| | 6.7 | 18.3 |
| Enzyme: | 12.5 | 35.0 |
| trypsin | | |
| Conditions: | | |
| pH8, 37° C. | | |
| $E_x$ = 420 nm | | |
| $E_m$ = 485 nm | | |

Where the FIG. 2 embodiment is used for enzyme analysis the liberated D compound therefrom is 7-amino-3-phenylcoumarin. This liberated D compound provides a good balance of properties for enzyme analyses (such as fluorescing wavelength, relative intensity and solubility), and has a particularly high level of fluorescent intensity. Table III, below, illustrates several properties of the liberated 7-amino-3-phenylcoumarin in comparison with two prior known coumarin derivative detector compounds.

TABLE III

| | Ex nm | Em nm | Rel. Int. | Sol.* mg/mL |
|---|---|---|---|---|
| (prior known) 7-amino-4-methyl coumarin | 345 | 435 | 2.8 | 5.1 × 10$^{-2}$ |
| (prior known) 7-amino-4-trifluoro-methyl coumarin | 390 | 500 | 1.0 | 1.7 × 10$^{-2}$ |
| (liberated from inventive substrate) 7-amino-3-phenyl coumarin | 368 | 472 | 4.0 | 1.2 × 10$^{-3}$ |

*in water as solvent, analogous to a buffered solution

It is believed that relatively low solubilities (not greater than about $1.2 \times 10^{-3}$ mg/mL in water or buffered solution) for the liberated D compounds are indicative of usefulness for enzyme localization within monodispersed cells. Liberated 7-amino-3-benzothiazolidyl coumarin, for example, has a solubility of about $1 \times 10^{-3}$ to about $1 \times 10^{-4}$ mg/mL in water.

Thus, it is believed that a synthetic substrate in accordance with the present invention having the structure illustrated by FIG. 4, below, (where the A moiety is as has been previously discussed) is particularly desirable for use to localize enzymes within active cells.

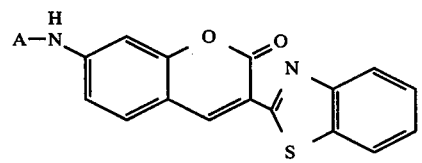

FIG. 4

SYNTHESES

For convenience, all syntheses are presented as specific examples, but it should be understood that variations in the methods, and particularly in the specific amino acids, polypeptides, and derivatives of the A moiety, will be apparent to those skilled in the art. All temperatures are degrees celsius.

EXAMPLE I 7-(Boc-L-leucinamido)-3-phenylcoumarin

To a solution of 1.16 g (5 mmol) of Boc-L-leucine and 0.70 ml (5 mmol) of triethylamine in 12 mL of tetrahydrofuran (dried over sodium/lead alloy) at −15° was added 0.66 mL (5 mmol) of i-butyl chloroformate. After 10 min., 1.19 g (5 mmol) of 7-amino-3-phenylcoumarin suspended in 6 mL of tetrahydrofuran was added. The mixture was stirred at −15° for 30 min. and then overnight at room temperature. The reaction mixture was then reduced to dryness on a rotary evaporator at 1.6 kPa and 60°. The residue was taken up in 100 mL of ethyl acetate, washed twice with 25-mL portions of 1 N aqueous sodium bicarbonate and twice with 25-mL portions of saturated sodium chloride, dried over anhydrous magnesium sulfate, filtered, and evaporated. The residue was dried overnight at room temperature and 3 Pa to yield 1.91 g. (84.8%) of crude product as a yellow foam which was purified by chromatography on a silica gel column eluted first with methylene chloride and then with 5% methanol in methylene chloride. Product recovery was 66.5%.

The analytical sample was further purified by thin layer chromatography on silica gel using methylene chloride as the developing solvent: R$_f$=0.17, mp=112.4°, [α]$_D^{21}$=−10.0° (c 1.8, MeOH); NMR (CDCl$_3$) δ(LeuCH$_3$)=0.98 D (6), H=4 Hz, δ(BocCH$_3$)=1.48 S (9), δ(LeuCH$_2$)=1.72 D (2), J=5 Hz, δ(LeuCH)=4.48 M (1), δ(LeuNH)=5.74 D (1), J=8 Hz, δ(ArH)=7.6 M (9), δ(CouNH)=9.8 S (1), IR (KBr) C=O=1710 cm$^{-1}$.

Anal. Calcd. for C$_{26}$H$_{30}$N$_2$O$_5$: C, 69.31; H, 6.71; N, 6.22. Found: C, 69.38; H, 6.88; N, 6.36.

EXAMPLE II 7-(L-Leucinamido)-3-phenylcoumarin/Hydrobromide

The product of Example I, above, (175.1 mg, 0.39 mmol) was dissolved at room temperature in 2 mL of 32% hydrobromic acid in acetic acid. After 10 min., 40 mL of 2/1 ether/petroleum ether was added. The precipitated solid was separated and dried overnight at room temperature and 5 Pa to yield a glassy, orange foam which was twice dissolved in 1 mL of absolute ethanol and reprecipitated by addition of 30 mL of ether. After drying overnight at room temperature and 5 Pa, there remained 73 mg (44.5%) of white solid; TLC (SiO$_2$: 10% methanol in methylene chloride) R$_f$=0.63; mp=190.1°; NMR (CD$_3$OD) δ(LeuCH$_3$)=1.08 D (6), J=5 Hz, δ(LeuCH$_2$) 1.86 D (2), δ(LeuCH)=4.0 M (1), δ(ArH)=7.7 M (9); IR (KBr) C=O=1700 cm$^{-1}$.

Anal. Calcd. for C$_{21}$H$_{22}$N$_2$O$_3$.1.5HBr: C, 56.32; H, 5.29; N, 6.26. Found: C, 55.92; H, 5.22; N, 6.22.

EXAMPLE III 7-(L-Leucinamido)-3-phenylcoumarin Trifluoroacetate

The product of Example I, above, (191.5 mg, 0.43 mmol) was dissolved at room temperature in 2 mL of trifluoroacetic acid. After 2 hr, the excess trifluoroacetic acid was removed at 1.6 kPa and room temperature, and the residue was dried at 0.1 Pa overnight. The yield of pale yellow glass was quantitative. It was purified by dissolving in 1 mL of methanol and reprecipitating by adding 30 mL of ether; mp=155.6°; NMR (2/1 CDCl$_3$/CD$_3$OD) δ(LeuCH$_3$)=1.02 D (6), J=5 Hz, δ(LeuCH$_2$)=1.87 D (2), δ(LeuCH)=4.2 M (1), δ(ArH)=7.6 M (9).

Anal. Calcd. for C$_{23}$H$_{23}$F$_3$N$_2$O$_5$: C, 59.48; H, 4.99; N, 6.03. Found: C, 59.75; H, 5.22; N, 6.03.

EXAMPLE IV 7-(L-Leucinamido)-3-phenylcoumarin Hydrochloride

The product of Example III, above, was dissolved in 9/1 ether/methanol and treated with hydrogen chloride gas until no more solid precipitated. The solid was redissolved in methanol and precipitated by addition of ether and dried overnight at room temperature and 0.1 Pa; mp 256.3° with decomposition.

Anal. Calcd. for C$_{21}$H$_{22}$N$_2$O$_3$.1.15HCl.5H$_2$O: C, 64.12; H, 6.19; N, 7.12; Cl, 10.37. Found: C, 63.92; H, 6.10; N, 7.23; Cl, 10.14.

EXAMPLE V 7-(Z-L-Alaninamido)-3-phenylcoumarin

To a solution of 1.78 g (5 mmol) of Z-alanine in 8 mL of dimethylformamide (dried over 4A molecular sieve) at −15° was added 0.90 mL (8.1 mmol) of N-methylmorpholine and 1.0 mL (7.6 mmol) of i-butyl chloroformate. After stirring at −15° for 30 min., 1.19 g (5 mmol) of 7-amino-3-phenylcoumarin was added, and stirring was continued overnight while the bath warmed to room temperature. The reaction mixture was poured into 20 mL of 1 N aqueous sodium bicarbonate. The solid that precipitated was washed twice with 20-mL portions of water and dried overnight at room temperature and 1 Pa. After two recrystallizations from aqueous dimethylformamide it weighed 1.18 g (53.3%); mp 203.2°; TLC (SiO$_2$: 1% methanol in methylene chloride) R$_f$=0.22; NMR (DMSO-d$_6$) δ(CH$_3$)=1.35 D (3), J=7 Hz, δ(NH)=3.3 M (2), δ(CH)=4.3 M (1), δ(OCH$_2$)=5.06 S (2), δ(ArH)=7.7 M (14); IR (KBr) C=O=1710 cm$^{-1}$.

Anal. Calcd. for C$_{26}$H$_{22}$N$_2$O$_5$: C, 70.58; H, 5.01; N, 6.33. Found: C, 71.10; H, 4.96; N, 6.51.

EXAMPLE VI 7-(Di-Z-lysyl-L-alaninamido)-3-phenylcoumarin

Hydrogen gas was passed through a solution of 1.18 g (2.7 mmol) of the product from Example V, above, in 15 mL of dimethylformamide containing 237.8 mg of 5% palladium-on-carbon until TLC of an aliquot showed no further change (about 10 h). This solution was filtered and added to the mixed anhydride prepared at −15° from 3.11 g (7.5 mmol) of di-Z-L-lysine, 0.85 mL (7.7 mmol) of N-methylmorpholine, and 0.92 mL (7.0 mmol) of i-butyl chloroformate in 8 mL of dimethylformamide. After stirring for 3 h at −15°, the reaction mixture was poured into 200 mL of 1 N aqueous sodium bicarbonate. The product was taken up in 100 mL of ethyl acetate and washed twice with 25-mL portions of saturated sodium chloride solution. After drying over anhydrous magnesium sulfate, it was filtered and evaporated and dried overnight at room temperature and 3 Pa to yield 3.40 g (78.8%) of crude product, which was purified by thin layer chromatography on silica gel using 3% methanol in methylene chloride for development; TLC (SiO$_2$: 3% methanol in methylene chloride) R$_f$=0.20; NMR (CDCl$_3$) δ(CH$_3$+CH$_2$)=1.4 M, δ(OCH$_2$)=5.03 S (2) and 5.13 S (2), δ(ArH)=7.4 M; IR (KBr) C=O=1700 cm$^{-1}$.

EXAMPLE VII 7-(L-Lysyl-L-alaninamido)-3-phenylcoumarin Dihydrobromide Monohydrate The product from Example VI, above, (150.6 mg, 0.21 mmol) was dissolved in 3 mL of 32% hydrobromic acid in acetic acid. After 15 min at room temperature, 40 mL of ether was added, and the precipitated product was collected and dried overnight at room temperature and 10 Pa; weight 130.5 mg (99.1%). It was purified by dissolving in 1 mL of methanol and precipitating by adding 20 mL of ether. Four such treatments yielded colorless material melting with decomposition about 240°. Amino acid analysis showed 1.08 Lysine to 0.92 alanine.

Anal. Calcd. for C$_{24}$H$_{30}$Br$_2$N$_4$.H$_2$O: C, 46.76; H, 5.23; N, 9.09. Found: C, 46.46; H, 4.99; N, 8.88.

EXAMPLE VIII 7-(Z-L-Arginamido)-3-phenylcoumarin

Z-L-Arginine (5.80 g, 18.8 mmol), P-toluenesulfonic acid monohydrate (3.58 g, 18.8 mmol), and 7-amino-3-phenylcoumarin (4.08 g, 17.2 mmol) were dissolved in 40 ml of dimethylformamide with stirring. N-Ethoxycarbonyl-2-ethoxy-1,2-dihydroquinoline (4.42 g, 17.9 mmol) was added and the reaction was allowed to proceed for three days at room temperature. The resulting suspension was filtered and the filtrate was evaporated in vacuo leaving a yellow oil that was taken up in 1500 ml of ethyl acetate/water (2:1) and shaken. The aqueous layer was removed and the ethyl acetate layer was washed twice with 500 ml volumes of water. The product precipitated in the ethyl acetate layer during the washing procedure and was collected by filtration, washed with ethyl acetate, and dried yielding 4.06 g (33.7%) of product as the p-toluenesulfonate salt; mp 221°; TLC (S$_i$O$_2$: ethyl acetate/2-butanone/formic acid/water-5:3:1:1) Rf=0.63.

Anal. Calcd. for $C_{36}H_{37}N_5O_8S.0.5H_2O$: C, 61.01; H, 5.40; N, 9.88; S, 4.52. Found C, 61.04; H, 5.30; N, 10.18; S, 4.60. Treatment of the above material with hydrogen chloride in acetic acid and precipitation with ether gave the more water soluble hydrochloride salt of I; mp 179°; $[\alpha]_D^{24}$ −24° (c 2.5, CH$_3$OH).

Anal. Calcd. for $C_{29}H_{30}O_5N_5Cl$: C, 61.75; H, 5.36; N, 12.42; Cl, 6.29. Found: C, 61.56; H, 5.56; N, 12.34; Cl, 6.38.

EXAMPLE IX

7-(Benzoyl-L-arginamido)-3-phenylcoumarin

The hydrochloride salt from Example VIII, above (0.247 g, 0.438 mmol), was treated with 3 ml of 32% hydrogen bromide in acetic acid for 75 min at room temperature. Addition of 70 ml ether gave crude 7-(L-arginamido)-3-phenylcoumarin dihydrobromide that was precipitated twice from methanol/ether yielding 0.221 g (91%) of an off white powder: mp 168°; TLC (SiO$_2$: ethyl acetate/2-butanone/formic acid/water-5:3:1:1) Rf=0.30. This material, without further purification, was dissolved in 4 ml of dry pyridine containing 0.11 ml (0.80 ml) of triethylamine and 0.436 g (1.99 mmol) of N-benzoyloxy-succinimide. The reaction proceeded overnight at room temperature. The pyridine was removed in vacuo and the crude product was purified by preparative layer chromatography on silica gel with several developments in ethyl acetate/formic acid/water (32:1:1). The purified material was taken up in 1000 ml ethyl acetate/1-butanol (1:1) and washed with 200 ml volumes of N HCl, brine (3x), and water (2x). The organic layer was evaporated in vacuo yielding 0.139 g (65.4%) of II as the hydrochloride salt: mp 251°; TLC (SiO$_2$: ethyl acetate/2-butanone/formic acid/water-5:3:1:1) Rf=0.67.

Anal. Calcd. for $C_{28}H_{28}ClN_5O_4.4C_4H_9OH$: C, 61.69; H, 5.84; N, 12.15; Cl, 6.15. Found: C, 61.77; H, 5.81; N, 11.86; Cl, 6.52.

EXAMPLE X

7-(Z-Glycylglycyl-L-arginamido)-3-phenylcoumarin 7-(L-Arginamido)-3-phenylcoumarin dihydrobromide (0.462 g, 0.832 mmol), prepared as previously described, was dissolved in 4 ml of pyridine containing triethylamine (0.233 ml, 1.66 mmol) and Z-glycylglycine N-hydroxysuccinimide ester (0.908 g, 2.50 mmol). The reaction proceeded one day at room temperature. The crude reaction mixture was twice subjected to preparative layer chromatography on silica gel using ethyl acetate/pyridine/formic acid/water (12:4:2:1) and then ethyl acetate/formic acid/water (16:1:1). The purified compound was taken up in 200 ml ethyl acetate/1-butanol (1:1) and washed with 70 ml volumes of N HCl, brine (3x) and water (2x). The organic layer was evaporated in vacuo yielding 0.209 g (34.8%) of product as the hydrochloride salt: mp 135°; TLC (S$_i$O$_2$: ethylacetate/2-butanone/formic acid/water-5:3:1:1) Rf=0.54, Amino acid analysis: glycine 2.02, arginine 0.98.

Anal. Calcd. for $C_{33}H_{36}N_7O_7.1.3HCl.0.5C_7H_9OH$: C, 57.89; H, 5.73; N, 13.50; Cl, 6.35. Found: C, 57.64; H, 5.53; N, 13.44; Cl, 5.97.

The p-toluenesulfonate salt of the product was also prepared: mp 166°.

Anal. Calcd. for $C_{40}H_{43}N_7O_{10}S.1.2C_4H_9OH$: C, 59.60; H, 6.14; N, 10.86; S, 3.55. Found: C, 59.97; H, 6.01; N, 11.14; S, 3.42.

EXAMPLE XI

7-(4-NO$_2$-Z-Glycylglycyl-L-arginamido)-3-phenylcoumarin 7-(L-Arginamido)-3-phenylcoumarin dihydrobromide (0.156 g, 0.281 mmol), triethylamine (0.039 ml, 0.281 ml), 4-NO$_2$-Z-glyclyglycine (0.088 g, 0.281 mmol), and N-ethoxycarbonyl-2-ethoxy-1,2-dihydroquinoline (0.076 g, 0.309 mmol) were allowed to react in 4 ml of dimethylformamide for 16 h at room temperature. The dimethylformamide was removed in vacuo and the resulting reaction mixture was subjected to preparative layer chromatography on silica gel using ethyl acetate/formic/water (16:1:1). The purified material was taken up in 200 ml of ethyl acetate/1-butanol (1:1) and washed with 40 ml volumes of N HCl, brine (3x) and water (2x). The organic layer was evaporated in vacuo yielding 0.123 g (60.5%) of product as the hydrochloride salt: mp 214°; TLC (S$_i$O$_2$: ethyl acetate/2-butanone/formic acid/water-5:3:1:1) Rf=0.61; amino acid analysis: glycine 2.06, arginine 0.94.

Anal. Calcd. for $C_{33}H_{34}N_8O_9.1.4HCl.0.7C_4H_9OH$: C, 54.46; H, 5.41; N, 14.19; Cl, 6.29. Found: C, 54.94; H, 5.54; N, 14.60; Cl, 6.93.

EXAMPLE XII

7-(4-NO$_2$-Z-L-Arginamido)-3-phenylcoumarin

The acylating reagent, 1-(4-nitrobenzyloxycarbonyl)-benzotriazole, was prepared from 4-nitrobenzyl chloroformate and 1-hydroxybenzotriazole using a procedure analogous to that described for 1-benzoyloxybenzotriazole [M. Ueda, K. Okada, and Y. Imai, *J. Polym. Sci. Polym. Chem. Ed.*, 14, 2665 (1976)]: mp 184°; IR (KBr) C=O=1745 cm$^{-1}$. Hydrogenation of the p-toluenesulfonate salt from Example VIII (2.00 g, 2.86 mmol) and p-toluenesulfonic acid monohydrate (0.544 g, 2.86 mmol) over 5% palladium-on-carbon (1.00 g) in 70 ml of dimethylformamide for 4.5 h gave 7-(arginamido)-3-phenylcoumarin di-p-toluenesulfonate in essentially quantitative yield (2.24 g); TLC (S$_i$O$_2$: ethyl acetate/2-butanone/formic acid/water-5:3:1:1) Rf=0.27.

1-(4-Nitrobenzyloxycarbonyl)-benzotriazole (0.314 g, 1.00 mmol), 7-(arginamido)-3-phenylcoumarin di-p-toluenesulfonate (0.664 g, 0.900 mmol) and triethylamine (0.126 ml, 0.900 mmol) were reacted in 6 ml of dimethylformamide for 10 h at room temperature. The dimethylformamide was removed in vacuo and the resulting reaction mixture was subjected to preparative layer chromatography on silica gel using ethyl acetate/formic acid/water (16:1:1). The purified material was taken up in 500 ml ethyl acetate/1-butanol (1:1) and washed with 50 ml portions of N HCl, brine, water. The organic layer was evaporated in vacuo yielding 0.437 g (79.7%) of product as the monohydrochloride. Recrystallization from methanol-ethyl acetate afforded the product in 51.9% yield; mp 213°; TLC (S$_i$O$_2$: ethyl acetate/2-butanone/formic acid/water-5:3:1:1) Rf=0.65. $[\alpha]_D^{23}$ −17° (c 1.2, CH$_3$OH).

Anal. Calcd. for C$_{29}$H$_{29}$O$_7$N$_6$Cl.CH$_3$OH: C, 56.21; H, 5.19; N, 13.11; Cl, 5.53. Found: C, 56.29; H, 4.80; N, 13.39; Cl, 5.09.

EXAMPLE XIII 7-(Z-L-Alaninamido)-3,4-benzocoumarin

To a solution of 1.78 g (5 mmol) of Z-alanine in 8 mL of dimethylformamide (dried over 4A molecular sieve) at −15° was added 0.90 mL (8.1 mmol) of N-methylmorpholine and 1.0 mL (7.6 mmol) of i-butyl chloroformate. After stirring at −15° for 30 minutes, 0.92 g (4.4 mmol) of 7-amino-3,4,benzocoumarin was added, and stirring was continued overnight while the bath warmed to room temperature. The reaction mixture was poured into 20 mL on 1 N aqueous sodium bicarbonate. The solid that precipitated was removed, washed twice with 20 mL portions of water and dried overnight at room temperature and 1 Pa. The residue was recrystallized twice from aqueous dimethylformamide; weight 1.18 g (65.0%); decomposes above 250° without melting; TLC (SiO$_2$: 1% methanol in methylene chloride) R$_f$=0.20; NMR (DMSO-d$_6$) $\delta$(CH$_3$)=1.37 M (3), $\delta$(NH)=3.3 M (2), $\delta$(CH)=4.2 M (1), $\delta$(OCH$_2$)=5.1 M (2), $\delta$(ArH)=7.8 M (12); IR (KBr) C=O=1700 cm$^{-1}$.

Anal. Calcd. for C$_{24}$H$_{20}$N$_2$O$_5$: C, 69.22; H, 4.84; N, 6.73. Found: C, 69.75; H, 4.76; N, 6.57.

EXAMPLE XIV 7-(Di-Z-L-lysyl-L-alanimamido)-3,4-benzocoumarin

Hydrogen gas was passed through a solution of 1.15 g (2.8 mmol) of the product from Example XIII, above, in 25 mL of dimethylformamide containing 244.5 mg of 5% palladium-on-carbon until TLC of an aliquot showed no further change (about 7 hr). This solution was centrifuged and the supernate was added to the mixed anhydride prepared at −15° from 3.11 g (7.5 mmol) of di-Z-lysine, 0.85 mL (7.7 mmol) of N-methylmorpholine, and 0.92 mL (7.0 mmol) of i-butyl chloroformate in 8 mL of dimethylformamide. After stirring for 3 h at −15°, the reaction mixture was poured into 200 mL if 1 N aqueous sodium bicarbonate. The product was taken up in 100 mL of ethyl acetate and washed twice with 25-mL portions of saturated sodium chloride solution. The wet ethyl acetate solution was evaporated, and the residue was dried overnight at room temperature and 10 Pa to give 4.24 g (89.2%) of crude product, which was purified by thin layer chromatography on silica gel using 3% methanol in methylene chloride for development; TLC (SiO$_2$: 3% methanol in methylene chloride) R$_f$=0.38; mp 208.2°; $[\alpha]_D^{24}$=−23.0°; (c 2.7, 9/1 chloroform/methanol); NMR (4/1 CDCl$_3$/CD$_3$OD) $\delta$(CH$_3$+CH$_2$)=1.4 M (11); $\delta$(OCH$_2$)=5.05 S (2) and 5.10 S (2), $\delta$(ArH)=7.6 M (17); IR (KBr) C=O=1700 cm$^{-1}$.

Anal. Calcd. for C$_{38}$H$_{38}$N$_4$O$_8$: C, 67.24; H, 5.64; N, 8.26. Found: C, 66.49; H, 5.44; N, 8.03.

EXAMPLE XV 7-(L-Lysyl-L-alaninamido)-3,4-benzocoumarin Hydrobromide

The product from Example XIV, above, (240.0 mg) (0.35 mmol) was treated at room temperature for 15 min with 3 mL of 32% hydrobromic acid in acetic acid. Crude product was precipitated by addition of 40 mL of ether. After drying overnight at room temperature and 15 kPa it was twice dissolved in 2 mL of methanol and precipitated by addition of 20 mL of ether; weight 214.2 mg; mp=242.4°; $[\alpha]_D^{24}$=−24.0° (c 2.1, MeOH); NMR (CD$_3$OD) $\delta$(CH$_3$+CH$_2$)=1.7 M (11), $\delta$(OCH$_2$)=1.53 S (2); $\delta$(ArH)=7.8 M (7); IR (KBr) C=O=1690 cm$^{-1}$.

Anal. Calcd. for C$_{22}$H$_{26}$N$_4$O$_4$.2.5HBr: C, 43.12; H, 4.69; N, 9.14. Found: C, 43.14; H, 4.64; N, 8.98.

We claim:

1. A synthetic substrate, useful for enzyme analysis, represented by A-D comprising:

an A moiety and a D moiety, said A and D moieties of said A-D bonded together by an enzyme hydrolyzable bond, said A moiety selected from the group consisting of Leu, Ala, Arg, Lys-Ala, Gly-Gly-Arg, salt forms thereof and blocking groups thereon, said A moiety determining an enzyme specificity of at least one enzyme for said synthetic substrate, said D moiety being a coumarin derivative defining a 3 position carbon and a 4 position carbon and having an electron withdrawing group substituted at said 3 position carbon or fused at said 3 and 4 position carbons and selected from the group consisting of

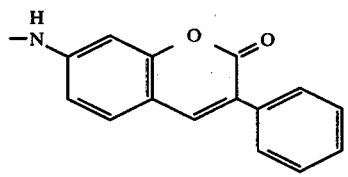

and

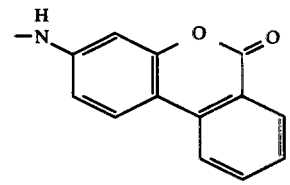

* * * * *

United States Patent and Trademark Office
CERTIFICATE OF CORRECTION

PATENT NO. : 4,388,233
DATED : Jun. 14, 1983
INVENTOR(S) : Bissell et al.

It is certified that error appears in the above—identified patent and that said Letters Patent is hereby corrected as shown below:

Col. 8, line 55, "$C_{24}H_{30}Br_2N_4 \cdot H_2O$" should be "$C_{24}H_{30}Br_2N_4O_4 \cdot H_2O$".

Signed and Sealed this

Twentieth Day of December 1983

[SEAL]

Attest:

GERALD J. MOSSINGHOFF

Attesting Officer

Commissioner of Patents and Trademarks